US011759559B2

(12) United States Patent
Aldridge (10) Patent No.: US 11,759,559 B2
(45) Date of Patent: Sep. 19, 2023

(54) ADJUSTABLE SHUNT PEDIATRIC/NEONATAL ECMO CIRCUIT

(71) Applicant: Alfred Lee Aldridge, Albuquerque, NM (US)

(72) Inventor: Alfred Lee Aldridge, Albuquerque, NM (US)

(*) Notice: Subject to any disclaimer, the term of this patent is extended or adjusted under 35 U.S.C. 154(b) by 244 days.

(21) Appl. No.: 17/376,529

(22) Filed: Jul. 15, 2021

(65) Prior Publication Data

US 2022/0241577 A1    Aug. 4, 2022

Related U.S. Application Data

(60) Provisional application No. 63/144,675, filed on Feb. 2, 2021.

(51) Int. Cl.
| | |
|---|---|
| *A61M 1/16* | (2006.01) |
| *A61M 60/38* | (2021.01) |
| *A61M 60/851* | (2021.01) |
| *A61M 60/279* | (2021.01) |
| *A61M 60/232* | (2021.01) |
| *A61M 60/113* | (2021.01) |

(52) U.S. Cl.
CPC .......... *A61M 60/38* (2021.01); *A61M 1/1698* (2013.01); *A61M 60/113* (2021.01); *A61M 60/232* (2021.01); *A61M 60/279* (2021.01); *A61M 60/851* (2021.01)

(58) Field of Classification Search
CPC .............. A61M 1/1698; A61M 1/3603; A61M 1/3659; A61M 1/3666; A61M 1/367; A61M 1/3672; A61M 39/10; A61M 2240/00
See application file for complete search history.

(56) References Cited

U.S. PATENT DOCUMENTS

| | | | | |
|---|---|---|---|---|
| 5,104,373 A | * | 4/1992 | Davidner | A61M 1/3603 604/6.08 |
| 5,391,142 A | * | 2/1995 | Sites | A61M 1/3603 604/6.14 |
| 2004/0184953 A1 | * | 9/2004 | Litzie | A61M 60/113 604/6.14 |
| 2013/0345675 A1 | * | 12/2013 | Zager | A61M 5/44 604/151 |

* cited by examiner

*Primary Examiner* — Ariana Zimbouski
(74) *Attorney, Agent, or Firm* — V Gerald Grafe (57) ABSTRACT

Embodiments of the present invention provide an extra corporeal membrane oxygenation circuit, wherein a pump communicates blood from a patient to an oxygenator and thence back to the patient, comprising: (a) a medium diameter venous line configured to accept blood from the patient and communicate the blood to the pump; (b) a medium diameter arterial line configured to accept blood from the oxygenator and communicate the blood to the patient; (c) one or more shunts connected in a series, where each shunt comprises a medium diameter input connected to a medium diameter output, where the medium diameter output is configured to connect to a medium diameter input of a successive shunt; a small diameter outlet between the medium diameter input and the medium diameter output; and a stopcock connected to the small diameter output such that flow out of the small diameter outlet can be controlled by the stopcock; wherein a first of such shunts is connected to accept blood from the venous line in parallel with the pump and wherein a last of such shunts is connected to communicate blood to the arterial line.

10 Claims, 6 Drawing Sheets

ADJUSTABLE SHUNT PEDIATRIC/NEONATAL ECMO CIRCUIT

TECHNICAL FIELD

The subject invention relates to an Extra Corporeal Membrane Oxygenation apparatus of particular use with pediatric and neonatal applications.

BACKGROUND ART

ECMO (Extra Corporeal Membrane Oxygenation) is a device used to support a patient's oxygenation when needed for pulmonary failure, or used to support both cardiac and pulmonary functions when heart failure and pulmonary dysfunction are present. These devices remove venous (de-oxygenated) blood from the patient via a placed cannula (or multiples), pass the blood through an artificial lung (membrane), and return the oxygenated blood to the patient via a second cannula. These devices are comprised of the tubing set (circuit), the oxygenator, a pump, a heater, and associated monitoring devices. ECMO can be used for durations of one day to over a month, depending upon the patient progress.

ECMO is used to support patients who present with pulmonary disease, and/or cardiac dysfunction. ECMO is also used to support post-surgical patients who require a lengthier recovery until their own organs can fully support them. ECMO devices may be initiated in the operating room, emergency room, or in the Intensive Care Unit (ICU).

Pediatric ECMO, an application where the present invention has particular utility, uses small components which are more appropriately sized to each patient. Smaller patients require lower blood flow rates than adults. Low blood flow rates present challenges in prevention of thrombus (clotting) in the ECMO circuit, as higher blood flow rates help to avoid areas of stasis in the circuit. While most ECMO patients receive anticoagulant medications to allow their blood to pass through the ECMO circuit, the level of anticoagulation is a greater challenge in the pediatric application. Minimal levels of anticoagulant are often used in neonates, as the fragility of their cerebral circulation can allow "brain bleeds" with anticoagulant therapy. Low levels of anticoagulant require closer monitoring of the ECMO circuit, as formation of clot may occur and require a change-out of the entire circuit. Changing the circuit results in an interruption of support, so efforts are made to avoid this procedure.

Figure 5:
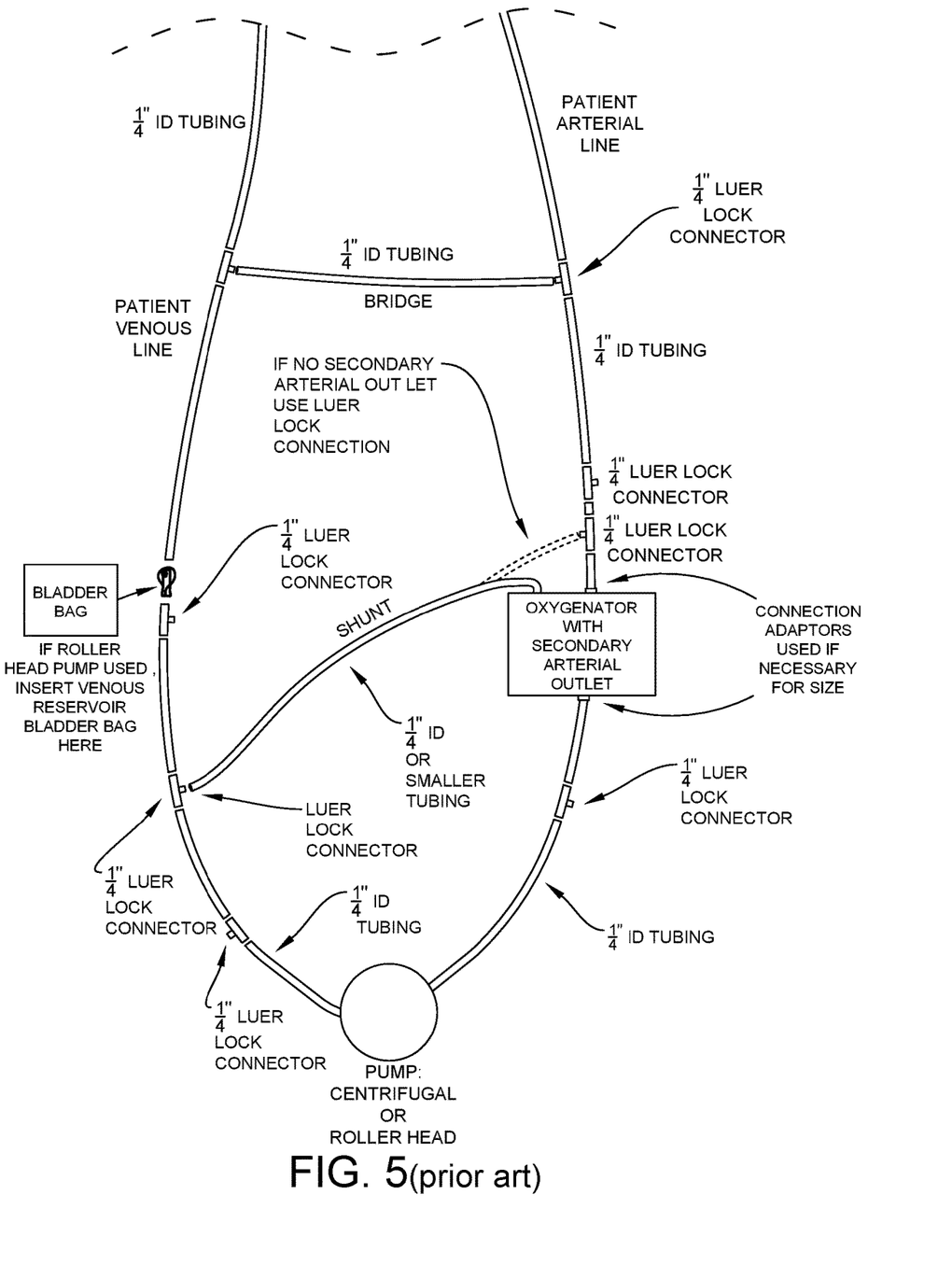
FIG. 5 is a schematic illustration of a conventional circuit.

Some ECMO circuitry has begun to incorporate a "shunt", which is an extra blood path that recirculates blood from the oxygenator back into the device by dividing the blood flow between the patient and the shunt. This adaptation allows greater overall blood flow through the oxygenator and helps to avoid the formation of clot in the device. The current implementation of shunts has been limited to small Luer fittings which support up to approximately 0.5 liters/minute of blood flow at their attachment points. This amount of flow, coupled with the flow to the patient, still falls near the minimum recommended flow range for many of the common oxygenators used in pediatric ECMO circuits. The lack of higher flow rates may lead to premature clotting (deposition of thrombus) in the oxygenator, and require circuit replacement. FIG. 5 is a schematic illustration of a representative contemporary ECMO circuit.

Current ECMO circuit designs also often have many connectors in the patient blood path, which are used for blood sampling, hookup of IV medications, etc. At low blood flow rates, each of these connectors also offers a location for thrombus to be deposited.

There exists a need for pediatric ECMO circuitry which allows higher blood flow through the oxygenator/pump section of the device. Achieving greater blood flow in the shunt allows for greater blood flow in the components of the ECMO circuit, while keeping the requisite blood flow to the patient at prescribed levels. There is also a need for a circuit design which eliminates as many connectors in the patient blood path as possible. Circuit replacement during an ECMO run typically results in an inflammatory reaction which produces a lengthier recovery or morbidity/mortality in some cases. All means safe and possible need to be employed to prevent unnecessary interruption of ECMO support. The present invention addresses these concerns.

DESCRIPTION OF INVENTION

Embodiments of the present invention provide an extra corporeal membrane oxygenation circuit, wherein a pump communicates blood from a patient to an oxygenator and thence back to the patient, comprising: (a) a venous subsystem comprising a medium diameter venous line configured to accept blood from the patient, wherein the venous subsystem is configured to communicate the blood to the pump; (b) a medium diameter arterial line configured to accept blood from the oxygenator and communicate the blood to the patient; (c) one or more shunts connected in a series, where each shunt comprises a medium diameter input connected to a medium diameter output, where the medium diameter output is configured to connect to a medium diameter input of a successive shunt; a small diameter outlet between the medium diameter input and the medium diameter output; and a stopcock connected to the small diameter output such that flow out of the small diameter outlet can be controlled by the stopcock; wherein a first of such shunts is connected to accept blood from the arterial line and wherein a last of such shunts is connected communicate blood to the venous subsystem.

In some embodiments, the pump is a roller pump, and wherein the venous subsystem comprises a venous bladder reservoir bag connected between the patient and the pump, and wherein the last shunt is connected to communicate blood to the venous line between the venous bladder reservoir bag and the pump.

In some embodiments, the pump is a centrifugal pump.

In some embodiments, the input of each shunt comprises a length of ¼" ID tubing connected to a T connector via a Luer lock fitting, and the small diameter output of each shunt comprises a length of ⅛" ID tubing connected to the T connected via a Luer lock fitting, and the output of each shunt comprises a Luer lock fitting on the T connector; and wherein the first shunt is connected to accept blood from the arterial line via a length of ¼" ID tubing distinct from the lengths of ¼" ID tubing forming the inputs of the shunts.

In some embodiments, the output of the last shunt is connected to communicate blood to the venous subsystem via a Y connector having medium diameter ports connected to the venous line, the pump, and the output of the last shunt.

In some embodiments, the first of such shunts is connected to accept blood from the arterial line via a Y connector having a first large diameter port connected to the oxygenator, a first medium diameter port connected to the input of the first shunt, and a medium diameter port connected to the arterial line.

In some embodiments, the first of such shunts is connected to accept blood from the arterial line via medium diameter output port of the oxygenator, where the oxygenator has a large diameter output port connected to the arterial line.

In some embodiments, the venous subsystem comprises a large diameter pump line connected to the pump, and an interface element adapting the medium diameter venous line to the large diameter pump line.

In some embodiments, the large diameter is ⅜", the medium diameter is ¼", and the small diameter is ⅛".

In some embodiments, the venous subsystem comprises a Y connector having a medium diameter input port connected to the venous line, a medium diameter input port connected to the output of the las shunt, and a large diameter output port connected to the pump; and wherein the arterial line comprises a Y connector having a large diameter input port connected to the oxygenator, a medium diameter output port connected to the input of the first shunt, and a medium diameter output port connected to a medium diameter line configured to communicate blood to the patient.

MODES FOR CARRYING OUT THE INVENTION AND INDUSTRIAL APPLICABILITY

Current pediatric ECMO circuits use either centrifugal pumps or roller-head pumps. The figures present diagrams which detail the connection and design of the Adjustable Shunt in each application. The inventors have discovered particular combinations of equipment, including sizes, that together provide new capabilities and advantages not known in the art. While those skilled in the art will appreciate variations that are within the scope of the invention, note that the cooperation among the components is important to proper operation; the Adjustable Shunt Pediatric/Neonatal ECMO circuit described herein might NOT function as intended if the specifications are altered. Omission of any design specification might cause improper operation of the circuit. In the description, certain tubing sizes, e.g., ⅜", ¼", and ⅛", are recited. Other tubing sizes can be used, provided the relative flow rates correspond to those of the recited sizes, and provided the total volume of blood corresponds to that of the recited sizes. ⅜" tubing is the "large diameter" tubing; ¼" is the "medium diameter", and ⅛" is the "small diameter" in the descriptions that follow. The example embodiments assume construction using commonly available components; various of the standard components recited can be combined and implemented as single entities, e.g., a piece of tubing and a connector can be implemented as a single element.

In all the example embodiments presented, the design goals of higher overall blood flow through the oxygenator and reduction of connectors in the patient blood path are met.

Definitions. Certain terms can facilitate understanding of the present invention, as described below.

Common Circuit: this section of the ECMO circuit contains the pump and oxygenator where blood flow is highest. Oxygenators with ⅜" ID inlet and either (1) two separate ¼" ID outlets or (2) a ⅜" ID outlet should be used to receive all the advantages of this design.

Patient Circuit: this section of the ECMO circuit contains the tubing which carries blood flow to the patient from the oxygenator outlet and the tubing which returns blood to the venous circuit junction from the patient.

Shunt: this section contains the tubing and associated connectors which recirculate blood flow from the oxygenator outlet to the inlet of the pump.

Shunt Module: comprised of a short piece of ¼" ID tubing, a ¼" Luer Lock connector, a short "pigtail" of ⅛" ID tubing (terminated on one end in a male Luer Lock, and a female Luer Lock on the other end) and a high-flow stopcock connected to the female Luer Lock on the pigtail. A ¼" ID piece of tubing (Connection Tubing) can be included with each shunt module.

Connection Tubing: a short piece of ¼" ID tubing used to complete the hookup of the Adjustable Shunt to the circuit.

Pump Boot: 1 or 2 pieces of ⅜" ID tubing (according to pump type utilized) which attach the patient circuit and shunt to the blood path through the pump to the oxygenator.

Circuit Junction: Y connectors used to combine the blood return from the patient and the blood return from the shunt for entry into the pump, and to split the blood flow leaving the oxygenator between the patient circuit and the shunt. ⅜"×¼"×¼" Y connectors are used. Some oxygenators have a main ⅜" blood outlet and a secondary ¼" blood outlet, and the shunt may be connected directly to this smaller outlet. In this case, a short piece of ⅜" ID tubing is used with a ⅜"×¼" reducer connector to attach to the patient arterial line and no Y connector is needed. Other oxygenator designs may have 2 separate ¼" outlets, allowing the shunt and the patient arterial line to be directly connected to the respective outlets.

Advantages. Embodiments of the present invention offer advantages such as the following.

Minimal connectors in the patient blood path. Connection points are now located in the high-flow portion of the circuit (shunt) where thrombus formation is reduced/eliminated by higher blood flow.

Hookup of additional devices (CRRT/dialysis, IV medications, blood gas monitoring, etc.) is now simple and convenient on the available shunt connections. The high shunt flow ensures good mixing of delivered medications. No interruption of blood flow to the patient is necessary to perform hookups/additions to the shunt. Diversion of some blood flow from the main shunt to provide adequate flow to auxiliary shunts (off the main shunt) may be adjusted by use of simple clamps or electronic occluder devices.

Higher blood flow rates through the oxygenator help to prevent thrombus deposition on the membrane and delay the need for oxygenator replacement or complete circuit replacement.

Blood flow through the common circuit (⅜" tubing) allows shunt flow to be maintained while delivering flow rates through ¼" patient circuit lines which approach the maximum for that tubing size. Therefore, this circuit may be used on larger children than devices with smaller common circuits.

The Adjustable Shunt, with all associated devices attached, may be transferred to a replacement ECMO circuit (if change-out of existing circuit is required). This procedure eliminates potential hazards of air introduction and minimizes interruption of IV medications compared to assembling a new shunt and its associated hookups. The high blood flow rates through the shunt minimize the possibility that thrombus will deposit in the shunt, allowing it to be "reused" on a replacement circuit.

Figure 1:
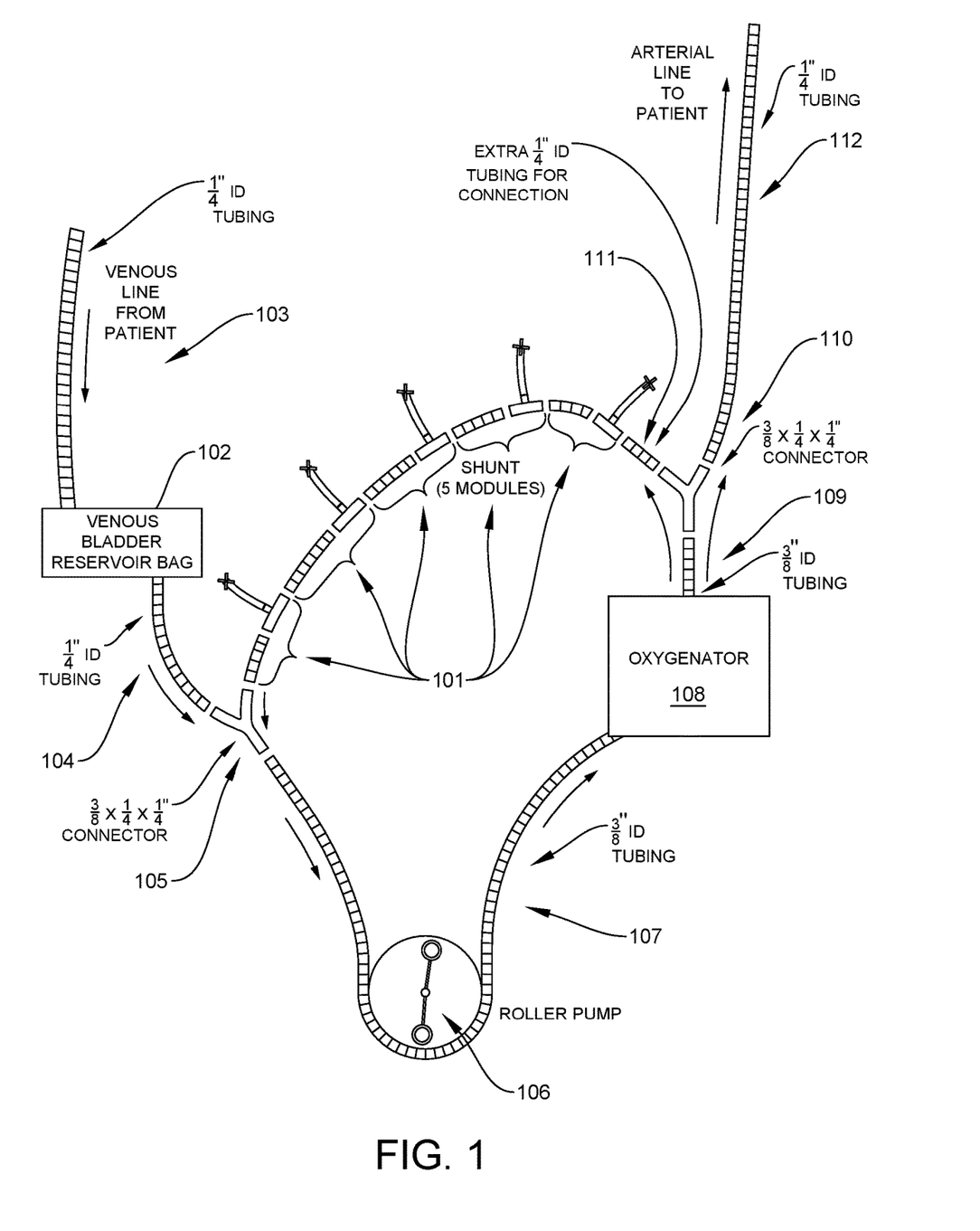
FIG. 1 is a schematic illustration of an example embodiment in a roller pump-based application.

Example Embodiment—Adjustable Shunt ECMO Circuit in a Roller Pump-Based Application In this example embodiment, a roller pump and a ⅜" inlet/outlet oxygenator are used for pediatric ECMO. FIG. 1 is a schematic illustration of an example embodiment in a roller pump-based application.

Pictured is the use of five Adjustable Shunt modules 101 to create a shunt with multiple attachment points for medication and associated devices. The Number of Adjustable Shunt modules utilized may be chosen by each institution according to their need for access points. Modules may be added or removed, with appropriate care by trained individuals, without interrupting blood flow to the patient by temporarily clamping the shunt line on both ends and adjusting roller pump flow accordingly while clamped.

Roller pump-based systems utilize a venous reservoir "bladder bag" 102 which allows for compliance in the system when patient blood volume and/or drainage via the venous line varies. The diagram shows the hookup location for the shunt (circuit junction) to create the entry to the common circuit.

¼" ID tubing provides a venous line 103 from the patient to the venous bladder reservoir bag 102. ¼" ID tubing connects the venous bladder reservoir bag 102 to a first ⅜"×¼"×¼" Y connector 105. The ⅜" port of the Y connector 105 is connected via ⅜" tubing to a roller pump 106. ⅜" ID tubing 107 connects the roller pup 106 output to an oxygenator 108. ⅜" ID tubing 109 connects the output of the oxygenator 108 to a second ⅜"×¼"×¼" Y connector 110. A ¼" port of the first Y connector 105 is connected to one or more shunts 101 (five shown in the figure). A final piece of ¼" ID tubing 111 connects the last shunt in the series to a ¼" port of the second Y connector 110. ¼" ID tubing 112 connects a ¼" port of the second Y connector 110 to provide an arterial line to the patient.

Blood flow is adjusted such that desired blood flow to the patient is achieved. Since the vascular resistance of the patient will be greater than that presented by the shunt, a large percentage of the total blood flow will be directed through the shunt. Patient monitoring will confirm adequate blood flow to the patient, and clamp-on flow probes may be used on the patient arterial line to assess blood flow at any time.

Figure 2:
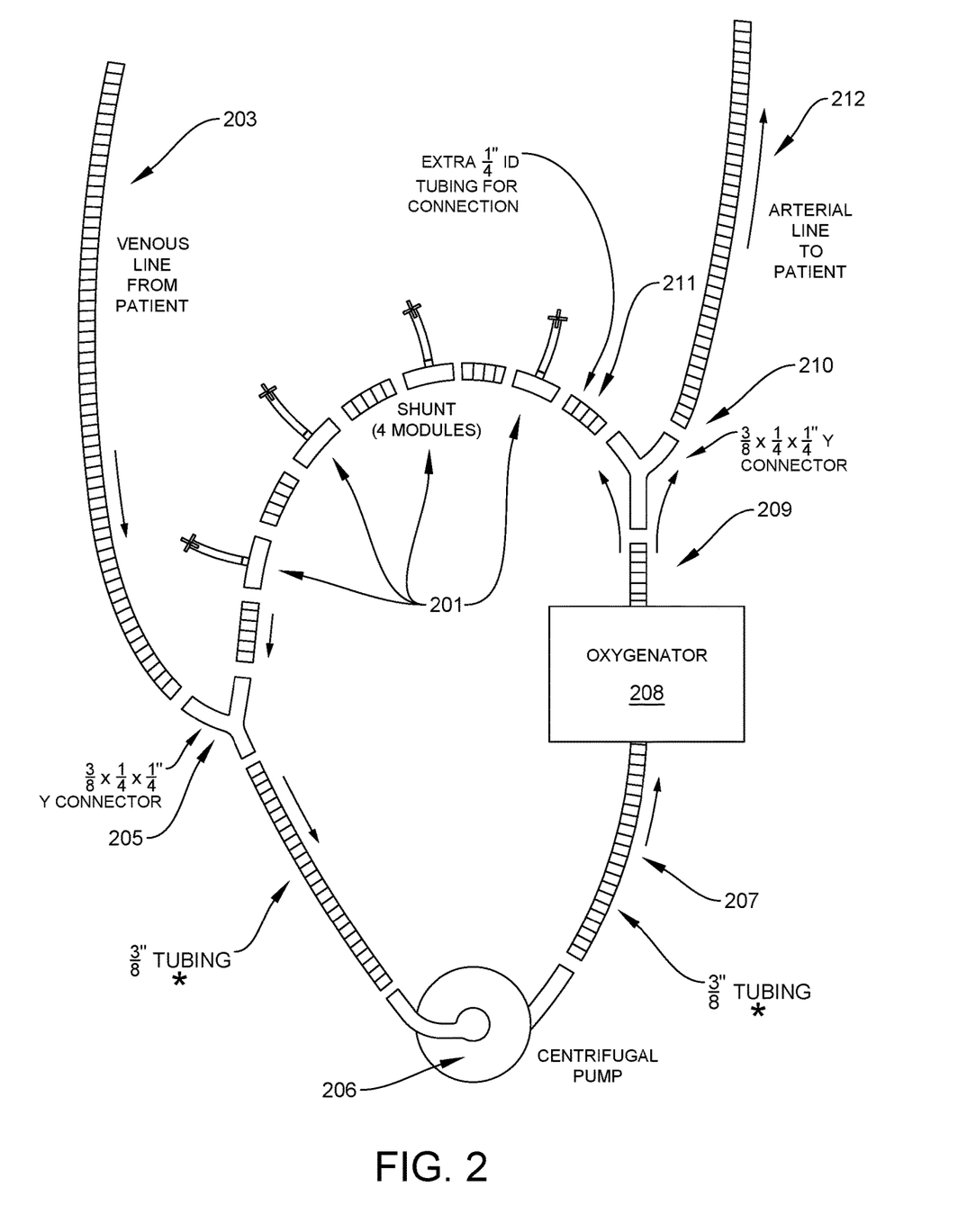
FIG. 2 is a schematic illustration of an example embodiment in a centrifugal pump-based application.
Figure 6:
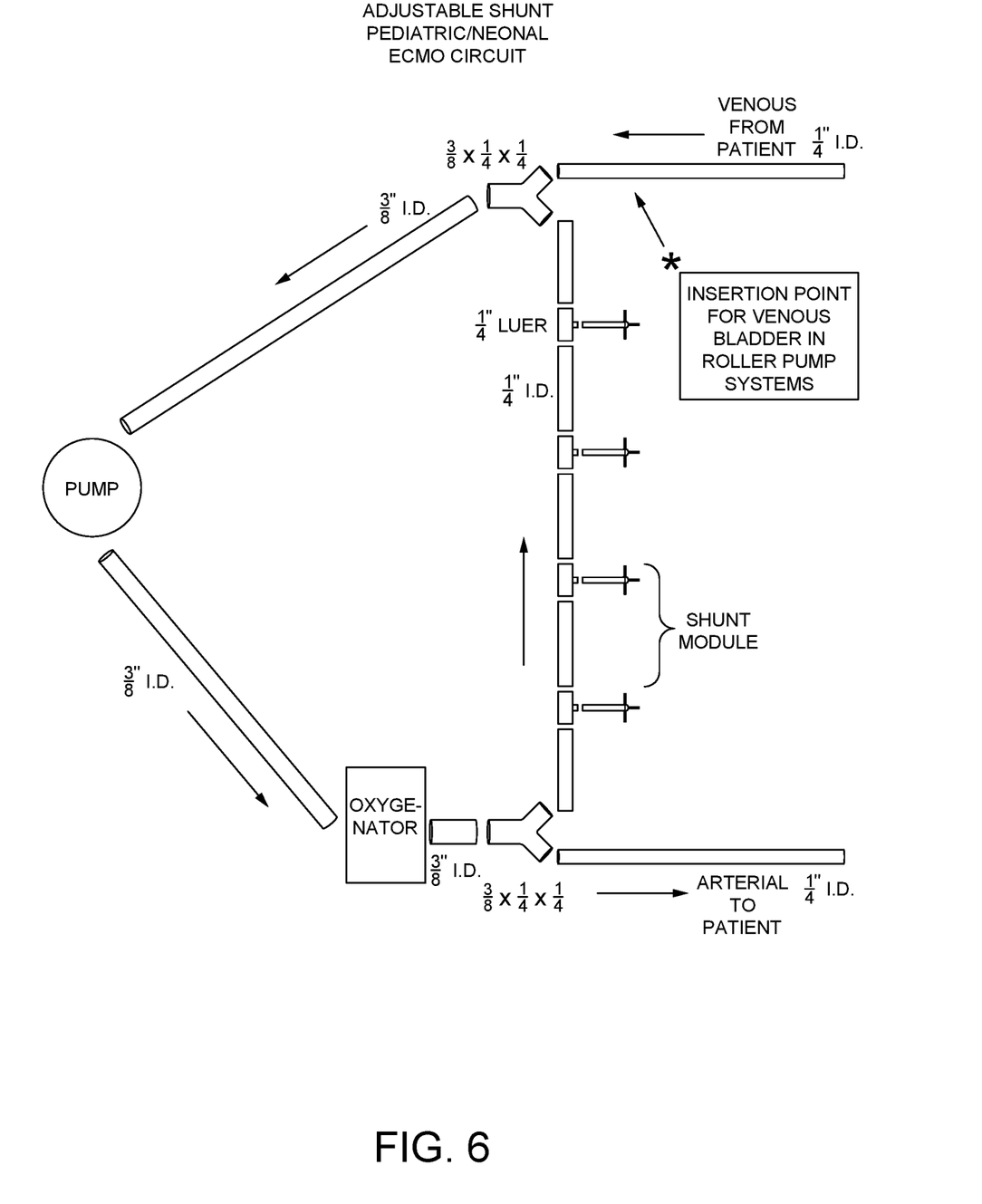
FIG. 6 is a schematic illustration of an example embodiment in a centrifugal pump-based application.

Example Embodiment—Adjustable Shunt ECMO Circuit a Centrifugal Pump-Based Application In this example embodiment, a centrifugal pump and oxygenator with ⅜" inlets and outlets are used for pediatric ECMO. FIG. 2 is a schematic illustration of an example embodiment in a centrifugal pump-based application. FIG. 6 is a schematic illustration of a similar example embodiment.

Pictured is the use of four Adjustable Shunt Modules to create a shunt with multiple attachment points for medication and associated devices. The Number of Adjustable Shunt modules utilized may be chosen by each institution according to their need for access points. Modules may be added or removed, with appropriate care by trained individuals, without interrupting blood flow to the patient by temporarily clamping the shunt line on both ends, and adjusting centrifugal pump flow accordingly while clamped.

Centrifugal pump-based systems auto-regulate their flow when patient volume status or drainage via the venous line varies. The diagram shows the hookup of the circuit components to complete the Adjustable Shunt ECMO circuit.

¼" ID tubing provides a venous line 203 from the patient to a first ⅜"×¼"×¼" Y connector 205. The ⅜" port of the Y connector 205 is connected via ⅜" tubing to a centrifugal pump 206. ⅜" ID tubing 207 connects the roller pup 206 output to an oxygenator 208. ⅜" ID tubing 209 connects the output of the oxygenator 208 to a second ⅜"×¼"×¼" Y connector 210. A ¼" port of the first Y connector 205 is connected to one or more shunts 201 (four shown in the figure). A final piece of ¼" ID tubing 211 connects the last shunt in the series to a ¼" port of the second Y connector 210. ¼" ID tubing 212 connects a ¼" port of the second Y connector 110 to provide an arterial line to the patient.

Blood flow is adjusted such that desired blood flow to the patient is achieved. Since the vascular resistance of the patient will be greater than that presented by the shunt, a large percentage of the total blood flow will be directed through the shunt. Patient monitoring will confirm adequate blood flow to the patient, and clamp-on flow probes may be used on the patient arterial line to assess blood flow at any time.

Features Common to Multiple Example Embodiments

ECMO circuits have traditionally incorporated a "bridge" between the arterial and venous lines in a location near the patient/cannulas. This "bridge" allowed for continuance of circuit blood flow while stopping blood flow to the patient for evaluation of cardiac/pulmonary recovery. The addition of this "bridge" required the use of additional connectors in the patient circuit in close proximity to the patient. The Adjustable Shunt Pediatric/Neonatal ECMO circuit uses the Adjustable Shunt as the "bridge" and eliminates the need for these additional connectors in the patient circuit, thereby reducing circuit complexity and eliminating redundancy.

As previously mentioned, the presence of connectors in the patient blood circuit poses a risk for thrombus deposition, especially in low-anticoagulation neonatal applications. The Adjustable Shunt Pediatric/Neonatal ECMO circuit reduces the number of connectors in the patient blood circuit to a minimum, while still allowing sufficient access points for connection to the circuit. *Institutions may choose to use additional connectors in the patient blood circuit according to their individual preferences and need for access.

The Adjustable Shunt and its circuit junctions allow for overall higher blood flow in the common circuit than traditional Luer-Lock connection-based shunt applications. Higher overall blood flow may reduce or eliminate the need to replace ECMO circuitry due to thrombus formation.

The use of the ⅜" ID tubing for the pump boot eliminates the need to create higher negative pressure in the pre-pump boot segment which would be required to combine the patient venous blood flow with the shunt flow in a ¼" size line. High negative venous pressure has been implicated in higher rates of hemolysis (destruction of red blood cells).

Figure 3:
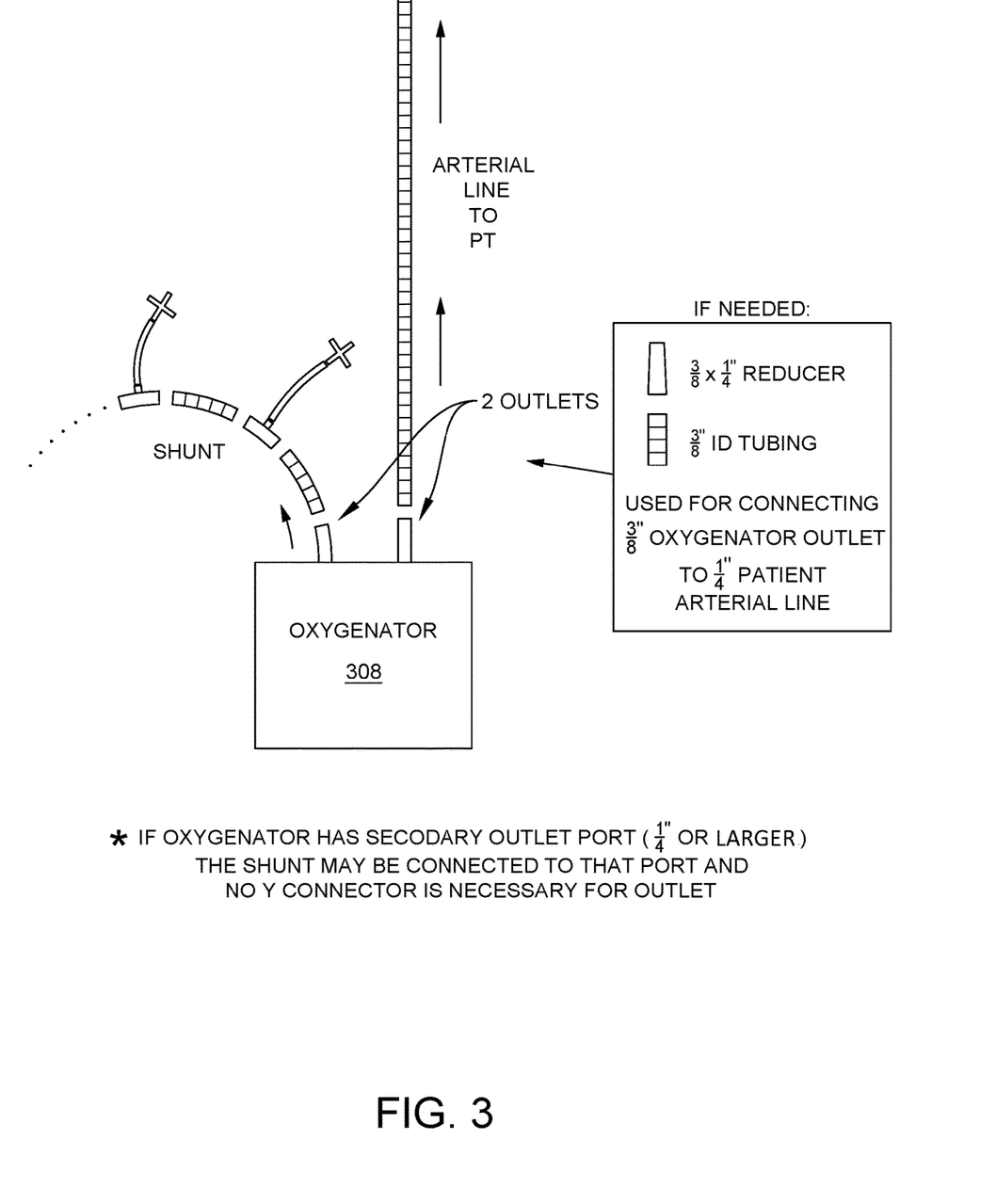
FIG. 3 is a schematic illustration of a variation when the oxygenator 308 has two outlets.

FIG. 3 is a schematic illustration of a variation when the oxygenator 308 has two outlets. The line from the shunt(s) and the arterial line can be connected directly to the two ports of the oxygenator 308, eliminating the need for the second Y connector. Reduction to ¼" ID can be needed, as shown in the figure, if the oxygenator port is ⅜" ID.

Figure 4:
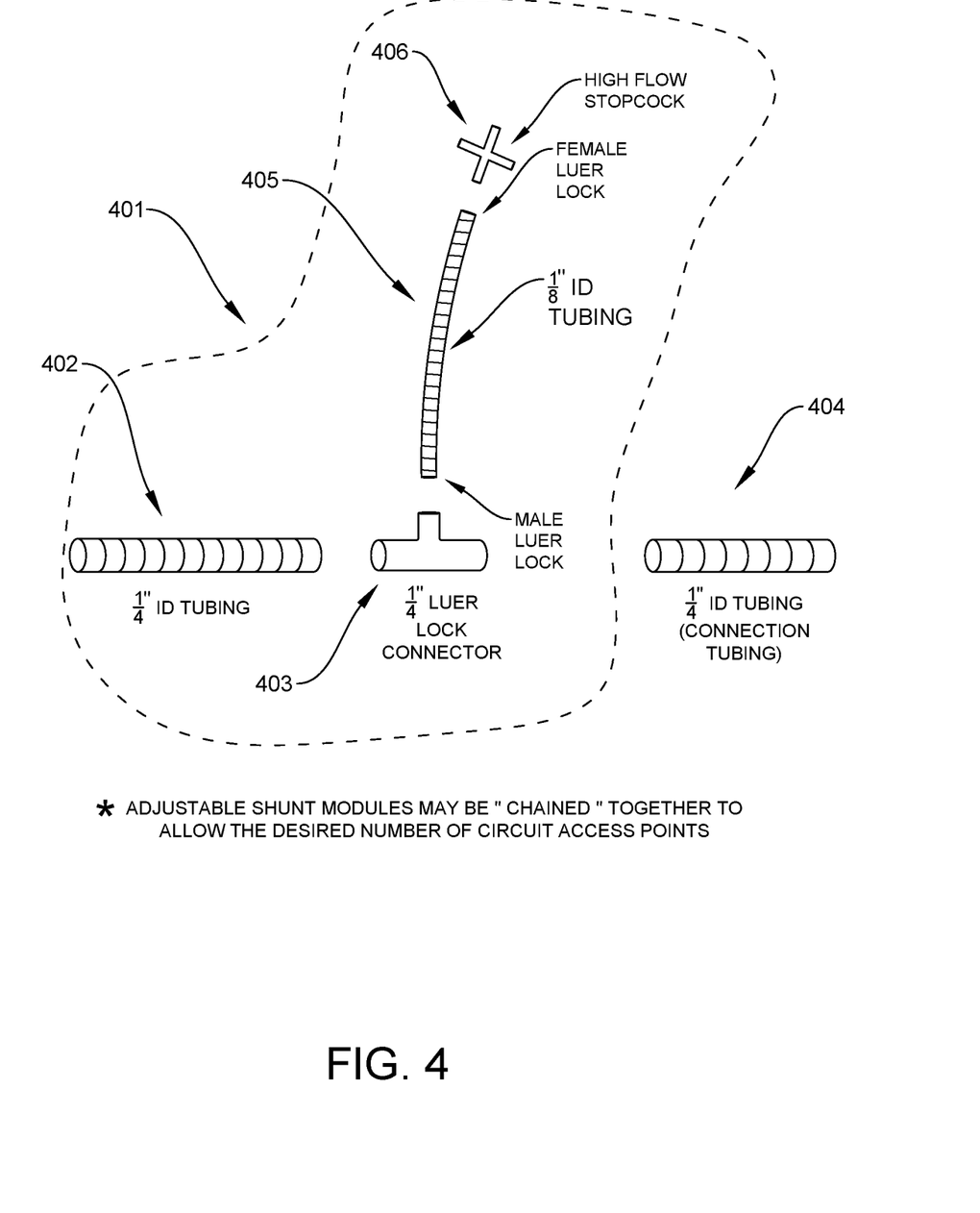
FIG. 4 is a schematic illustration of a shunt used in the example embodiments.

FIG. 4 is a schematic illustration of a shunt s used in the example embodiments. A section of ¼" ID tubing 402 is connected to a ¼" Luer lock T connector 403. A ⅛" port of the Luer lock T connector 403 is connected by ⅛" ID tubing to a high flow stopcock 406. This shunt can be repeated and chained together. The final shunt in the series can use ¼" tubing 404, if needed, to connect to the rest of the circuit.

The present invention has been described in connection with various example embodiments. It will be understood that the above description is merely illustrative of the applications of the principles of the present invention, the scope of which is to be determined by the claims viewed in light of the specification. Other variants and modifications of the invention will be apparent to those skilled in the art.

What is claimed is:

1. An extra corporeal membrane oxygenation circuit, wherein a pump is configured to communicate blood from a patient to an oxygenator and thence back to the patient, comprising:
   (a) a venous subsystem comprising a medium diameter venous line configured to accept blood from the patient, wherein the venous subsystem is configured to communicate the blood to the pump;
   (b) a medium diameter arterial line configured to accept blood from the oxygenator and communicate the blood to the patient;
   (c) two or more shunts connected in a series, where each of the two or more shunts comprises
   (c1) a medium diameter input connected to a medium diameter output, where the medium diameter output is configured to connect to a medium diameter input of a successive shunt in the series of said two or more shunts;
   (c2) a small diameter outlet between the medium diameter input and the medium diameter output; and
   (c3) a stopcock connected to the small diameter output such that flow out of the small diameter outlet can be controlled by the stopcock;
   wherein a first shunt in the series of said two or more shunts is connected to accept blood from the arterial line and wherein a last shunt in the series of said two or more shunts is connected to communicate blood to the venous subsystem, where the medium diameter is twice the small diameter.

2. The extra corporeal membrane oxygenation circuit of claim 1, wherein the pump is a roller pump, and wherein the venous subsystem comprises a venous bladder reservoir bag configured to be connected between the patient and the pump, and wherein the last shunt in the series of said two or more shunts is connected to communicate blood to the venous line between the venous bladder reservoir bag and the pump.

3. The extra corporeal membrane oxygenation circuit of claim 1, wherein the pump is a centrifugal pump.

4. The extra corporeal membrane oxygenation circuit of claim 1, wherein the input of each of the two or more shunts comprises a length of ¼" inner diameter tubing connected to a T connector via a Luer lock fitting, and the small diameter output of each shunt comprises a length of ⅛" inner diameter tubing connected to the T connector via a Luer lock fitting, and the output of each of the two or more shunts comprises a Luer lock fitting on the T connector; and wherein the first shunt in the series of said two or more shunts is connected to accept blood from the arterial line via a length of ¼" inner diameter tubing distinct from the lengths of ¼" inner diameter tubing forming the inputs of the two or more shunts.

5. The extra corporeal membrane oxygenation circuit of claim 1, wherein the output of the last shunt in the series of said two or more shunts is connected to communicate blood to the venous subsystem via a Y connector having medium diameter ports connected to the venous line, the pump, and the output of the last shunt.

6. The extra corporeal membrane oxygenation circuit of claim 1, wherein the first shunt in the series of said two or more shunts is connected to accept blood from the arterial line via a Y connector having a first large diameter port connected to the oxygenator, a first medium diameter port connected to the input of the first shunt in the series of said two or more shunts, and a medium diameter port connected to the arterial line, where the large diameter is 1.5 times the medium diameter.

7. The extra corporeal membrane oxygenation circuit of claim 1, wherein the first shunt in the series of said two or more shunts is connected to accept blood from the arterial line via medium diameter output port of the oxygenator, where the oxygenator has a large diameter output port connected to the arterial line, where the large diameter is 1.5 times the medium diameter.

8. The extra corporeal membrane oxygenation circuit of claim 1, wherein the venous subsystem comprises a large diameter pump line connected to the pump, and an interface element adapting the medium diameter venous line to the large diameter pump line, where the large diameter is 1.5 times the medium diameter.

9. The extra corporeal membrane oxygenation circuit of claim 1, wherein the medium diameter is ¼", and the small diameter is ⅛".

10. The extra corporeal membrane oxygenation circuit of claim 8, wherein the venous subsystem comprises a first Y connector having a medium diameter input port connected to the venous line, a medium diameter input port connected to the output of the last shunt in the series of said two or more shunts, and a large diameter output port connected to the pump; and wherein the arterial line comprises a second Y connector having a large diameter input port connected to the oxygenator, a medium diameter output port connected to the input of the first shunt in the series of said two or more shunts, and a medium diameter output port connected to a medium diameter line configured to communicate blood to the patient, where the large diameter is 1.5 times the medium diameter.

* * * * *